US00PP14180P29

(12) United States Plant Patent
Dümmen

(10) Patent No.: US PP14,180 P2
(45) Date of Patent: Sep. 30, 2003

(54) PETUNIA PLANT NAMED 'DUESURIMKAVE'

(50) Latin Name: *Petunia×hybrida*
Varietal Denomination: Duesurimkave

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 10/228,474

(22) Filed: Aug. 27, 2002

(51) Int. Cl.[7] ..... A01H 5/00
(52) U.S. Cl. ..... Plt./356
(58) Field of Search ..... Plt./356

(56) References Cited

PUBLICATIONS http://www.surfinia.com/2003/surfinia.html.*
UPOV ROM GTITM Computer Database, GTI JOUVE Retrieval Software 2002/06, citation(s) for 'Revolution'.*

* cited by examiner

*Primary Examiner*—Bruce R. Campbell
*Assistant Examiner*—W C Haas
(74) *Attorney, Agent, or Firm*—C. A. Whealy

(57) ABSTRACT

A new and distinct cultivar of Petunia plant named 'Duesurimkave', characterized by its compact, upright and outwardly spreading plant habit; freely basal branching; freely flowering habit; and single flowers that are light purple in color with dark purple-colored venation.

1 Drawing Sheet

BOTANICAL CLASSIFICATION/CULTIVAR DESIGNATION

*Petunia×hybrida* cultivar Duesurimkave.

BACKGROUND OF THE INVENTION

The present Invention relates to a new and distinct cultivar of Petunia plant, botanically known as *Petunia×hybrida*, and hereinafter referred to by the cultivar name Duesurimkave.

The new Petunia is a product of a planned breeding program conducted by the Inventor in Rheinberg, Germany. The objective of the breeding program is to create new freely branching Petunias with large flowers and attractive flower coloration.

The new Petunia originated from a cross pollination made by the Inventor in April, 1998 of an unidentified Petunia selection, not patented, as the female, or seed parent, with a proprietary Petunia selection identified as code number F-18-05, not patented, as the male, or pollen parent. The new Petunia was selected as a single plant from the resulting progeny of the cross-pollination by the Inventor in Rheinberg, Germany in June, 2000, on the basis of its attractive flower color.

Asexual reproduction of the new cultivar by terminal vegetative cuttings taken in Rheinberg, Germany since June, 2001, has shown that the unique features of this new Petunia are stable and reproduced true to type in successive generations.

SUMMARY OF THE INVENTION

Plants of the cultivar Duesurimkave have not been observed under all possible environmental conditions. The phenotype may vary somewhat with variations in environment such as temperature and light intensity without, however, any variance in genotype.

The following traits have been repeatedly observed and are determined to be the unique characteristics of 'Duesurimkave'. These characteristics in combination distinguish 'Duesurimkave' as a new and distinct cultivar:

1. Compact, upright and outwardly spreading plant habit.
2. Freely basal branching habit.
3. Freely flowering habit.
4. Single flowers that are light purple in color with dark purple-colored venation.

Compared to plants of the female parent, the unidentified selection, plants of the new Petunia differ in flower color. Compared to plants of the male parent, the selection F-18-05, plants of the new Petunia have larger flowers and differ in flower color.

Plants of the new Petunia can be compared to plants of the cultivar Surfinia Revolution, not patented. In side-by-side comparisons conducted in Rheinberg, Germany, plants of the new Petunia differed from plants of the cultivar Surfinia Revolution in the following characteristics:

1. Plants of the new Petunia were more compact than plants of the cultivar Surfinia Revolution.
2. Plants of the new Petunia were more freely branching than plants of the cultivar Surfinia Revolution.
3. Plants of the new Petunia had larger leaves than plants of the cultivar Surfinia Revolution.
4. Plants of the new Petunia were more freely flowering than plants of the cultivar Surfinia Revolution.
5. Plants of the new Petunia had larger flowers than plants of the cultivar Surfinia Revolution.
6. Flowers of plants of the new Petunia and the cultivar Surfinia Revolution differed slightly in color.
7. Plants of the new Petunia had longer peduncles than plants of the cultivar Surfinia Revolution.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph differ slightly from the color values cited in the detailed botanical description which accurately describe the colors of the new Petunia. The photograph comprises a top perspective view of typical flowers and leaves of 'Duesurimkave'.

DETAILED BOTANICAL DESCRIPTION

The cultivar Duesurimkave has not been observed under all possible environmental conditions. The phenotype may vary somewhat with variations in environment such as temperature and light intensity without, however, any variance in genotype.

The aforementioned photograph, following observations and measurements describe plants grown during the spring in Rheinberg, Germany, under commercial practice in a glass-covered greenhouse. Plants were about 16 weeks from cuttings and were grown in containers. During the production of the plants, day and night temperatures averaged 18° C. and light levels were about 4,500 lux. Plants were pinched once about three weeks after planting.

In the following description, color references are made to The Royal Horticultural Society Colour Chart, 1995 Edition, except where general terms of ordinary dictionary significance are used.

Botanical classification: *Petunia×hybrida* cultivar Duesurimkave.

Parentage:

*Female parent.*—Unidentified *Petunia×hybrida* selection, not patented.

*Male parent.*—Proprietary *Petunia×hybrida* selection identified as code number F-18-05, not patented.

Propagation:

*Type cutting.*—Terminal vegetative cuttings.

*Time to initiate roots.*—Summer: About 7 days at 20° C. Winter: About 10 days at 20° C.

*Time to develop roots.*—Summer: About 21 days at 20° C. Winter: About 28 days at 20° C.

*Root description.*—Fine, fibrous, white in color.

*Rooting habit.*—Freely branching.

Plant description:

*Form.*—Annual flowering plant; indeterminate; compact, upright and outwardly spreading; eventually cascading. Moderately vigorous.

*Usage.*—Appropriate for hanging baskets, window boxes, patio containers and landscape applications.

*Plant height.*—About 20 cm.

*Plant diameter.*—About 40 cm.

*Branching habit.*—Freely basal branching with about eight to ten lateral branches per plant.

*Lateral branches.*—Length: About 30 cm. Diameter: About 5 mm. Internode length: About 1.8 cm. Texture: Pubescent. Color: 144B.

*Foliage description.*—Arrangement: Before flowering, alternate; after flowering, opposite; simple. Quantity per lateral branch: About 16. Length: About 7.7 cm. Width: About 4 cm. Shape: Roughly spatulate. Apex: Obtuse. Base: Attenuate. Margin: Entire. Texture, upper and lower surfaces: Pubescent; leathery. Venation pattern: Pinnate. Color: Young and fully expanded foliage, upper surface: 137A. Young and fully expanded foliage, lower surface: 137C. Venation, upper and lower surfaces: 144B. Petiole length: About 7.3 mm. Petiole diameter: About 3 mm. Petiole color: 144B.

Flower description:

*Flower type and habit.*—Single rounded salverform flowers; flowers face mostly upward or outward; axillary; freely flowering, about four flowers and flower buds per lateral branch.

*Natural flowering season.*—Long day responsive; spring until frost in the autumn; flowering continuous. Plants start flowering about nine weeks after planting. Flowers persistent.

*Flower longevity on the plant.*—About five to seven days; flowers persistent.

*Fragrance.*—None detected.

*Flower size.*—Diameter: About 6.5 cm. Tube length: About 2.8 cm. Throat diameter, distal end: About 1.3 cm. Tube diameter, proximal end: About 4 mm.

*Flower buds.*—Length: About 3.2 cm. Diameter: About 7 mm. Shape: Ovoid. Color: 187B.

*Corolla.*—Quantity/arrangement: Five fused petals; funnelform. Petal length from throat: About 3.2 cm. Petal width: About 2.7 cm. Petal shape: Roughly spatulate. Petal apex: Obtuse. Petal margin: Entire; slightly ruffled. Petal texture, upper and lower surfaces: Smooth, velvety. Petal color: When opening and fully opened, upper surface: 71A; flower color does not fade with subsequent development. When opening and fully opened, lower surface: 77B. Flower throat (inside): 79A. Flower tube (outside): 79A. Venation, upper and lower petal surfaces: 79A. Venation, throat: 79A. Venation, tube: 79A.

*Sepals.*—Arrangement/appearance: Single whorl of five sepals fused at base, star-shaped. Length: About 1 cm. Width: About 2.5 mm. Shape: Strap-like; elongate. Apex: Rounded. Margin: Entire. Texture, upper and lower surfaces: Pubescent. Color: Upper surface: 137A. Lower surface: 137C.

*Peduncles.*—Length: About 4.5 cm. Width: About 1.25 mm. Angle: Erect to slightly bent. Strength: Moderately strong. Texture: Pubescent. Color: 144B.

*Reproductive organs.*—Stamens: Quantity per flower: About five. Anther shape: Ovoid. Anther length: About 3 mm. Anther color: 79D. Pollen amount: Abundant. Pollen color: 85B. Pistils: Quantity per flower: One. Pistil length: About 2.5 cm. Style length: About 1.8 cm. Style color: 145C. Stigma shape: Rounded. Stigma color: 139A. Ovary color: 144B.

*Seed/fruit.*—Seed nor fruit production has not been observed.

Disease/pest resistance: Plants of the new Petunia have not been noted to be resistant to pathogens or pests common to Petunia.

Temperature tolerance: Plants of the new Petunia have been observed to tolerate temperatures from 2 to 38° C.

It is claimed:

1. A new and distinct cultivar of Petunia plant named 'Duesurimkave', as illustrated and described.

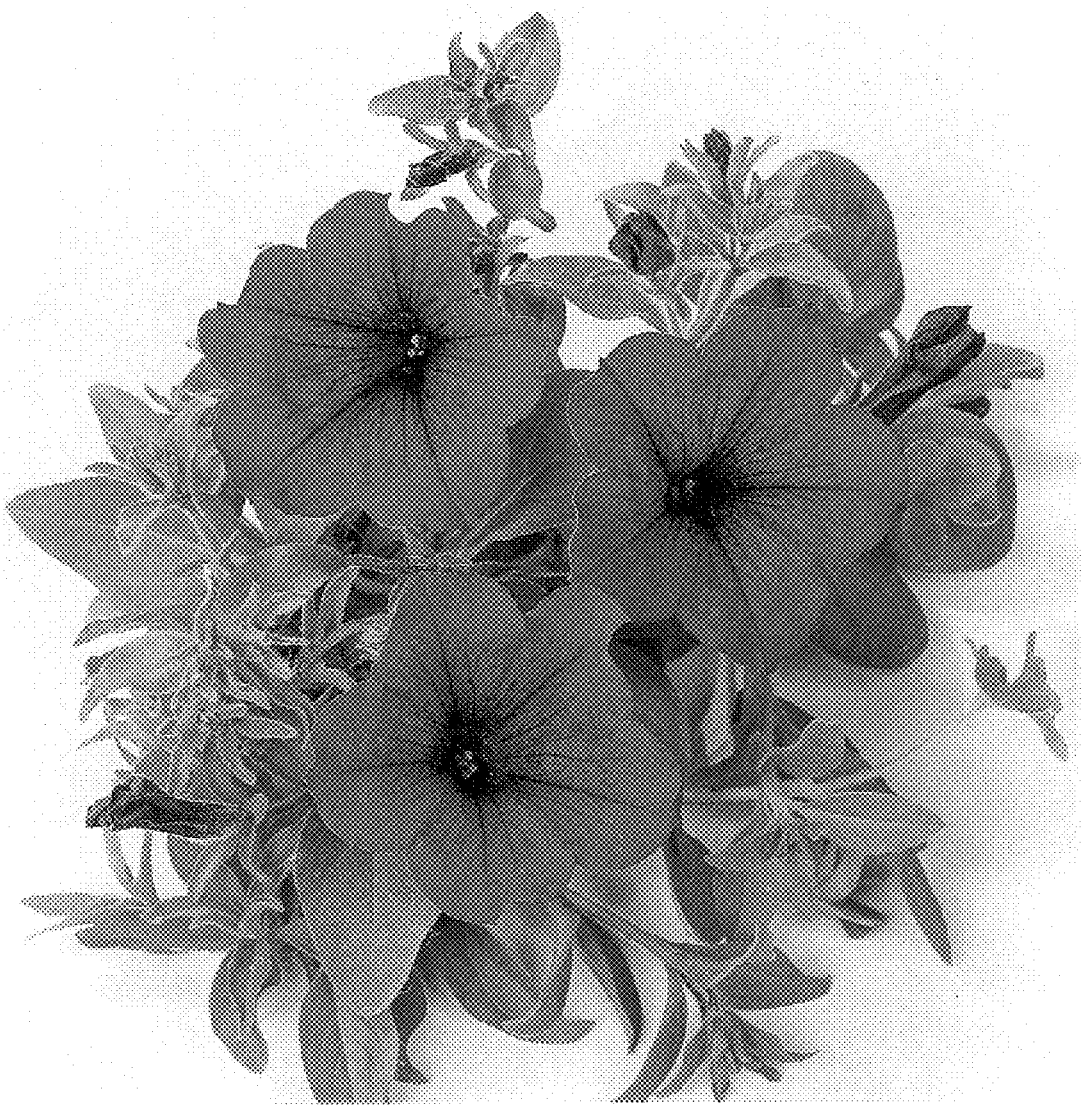

* * * * *